US 6,565,686 B2

(12) United States Patent
Bett et al.

(10) Patent No.: US 6,565,686 B2
(45) Date of Patent: *May 20, 2003

(54) INFRARED IMAGING TO DETECT COMPONENTS ON PERSONAL CARE ARTICLES

(75) Inventors: Thomas Arthur Bett, Oshkosh, WI (US); Jean Louise Krueger-Justinger, Neenah, WI (US); Tanakon Ungpiyakul, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/163,317

(22) Filed: Jun. 5, 2002

(65) Prior Publication Data

US 2002/0148567 A1 Oct. 17, 2002

Related U.S. Application Data

(60) Continuation of application No. 09/558,926, filed on Apr. 26, 2000, now Pat. No. 6,408,917, which is a division of application No. 09/190,692, filed on Nov. 12, 1998, now Pat. No. 6,224,699.

(51) Int. Cl.$^7$ .............................................. B32B 31/16
(52) U.S. Cl. ...................................... 156/64; 156/73.1
(58) Field of Search ......................... 156/64, 73.1, 163, 156/164, 229, 378, 494, 495, 510, 522, 580.1, 580.2

(56) References Cited

U.S. PATENT DOCUMENTS

| 4,680,205 A | 7/1987 | Lerner et al. ................. 428/29 |
| 4,837,715 A | 6/1989 | Ungpiyakul et al. ......... 364/552 |
| 4,969,037 A | 11/1990 | Poleschinski et al. ....... 358/106 |
| 5,200,023 A | 4/1993 | Gifford et al. ............... 156/626 |
| 5,235,515 A | 8/1993 | Ungpiyakul et al. ........ 364/469 |

(List continued on next page.)

FOREIGN PATENT DOCUMENTS

| EP | 0 842 765 A2 | 5/1998 | ............. B31B/1/74 |

OTHER PUBLICATIONS

Tivin, Paul, and Thomas C. Venable, "Infrared Imaging Enhances Manufacturing Operations". *Laser Focus World*, Aug./Sep. 1992, pp. 107–111.
Mitsubishi, "The High & The Mighty", Product Literature, (1 sheet) 1993.

(List continued on next page.)

*Primary Examiner*—James Sells
(74) *Attorney, Agent, or Firm*—Wilhelm Law Service; Thomas D. Wilhelm

(57) ABSTRACT

This invention pertains to fabricating composite personal care article products on a fabrication line, and sensing assembly quality characteristics of such personal care article products so fabricated, using infrared image sensing apparatus, and signal processing apparatus for processing the infrared energy so sensed, to fabricate visual displays of the composite images sensed by the infrared sensing apparatus. By using infrared imagery, and sensing the various temperatures of elements being placed and worked on the fabrication line, elements of the personal care articles which are hidden from visual observation can be sensed by sensing the infrared radiation emitted from such articles. Elements which are available for visual observation can likewise be sensed where temperature of such elements is suitable for detection, by infrared-sensitive receptors. Typically, a suitable infrared signature can be obtained without adding, to the elements whose quality is being assessed, any increment of heat for purposes of enhancing detection of such element or elements.

32 Claims, 7 Drawing Sheets

U.S. PATENT DOCUMENTS

| | | | |
|---|---|---|---|
| 5,286,543 A | 2/1994 | Ungpiyakul et al. | 428/74 |
| 5,359,525 A | 10/1994 | Weyenberg | 364/469 |
| 5,386,117 A | 1/1995 | Piety et al. | 250/330 |
| 5,399,016 A | 3/1995 | Martin | 374/7 |
| 5,458,062 A | 10/1995 | Goldberg et al. | 101/485 |
| 5,543,177 A | 8/1996 | Morrison et al. | 427/288 |
| 5,567,273 A | 10/1996 | Offerhaus et al. | 162/199 |
| 5,624,420 A | 4/1997 | Bridges et al. | 604/365 |
| 5,637,871 A | 6/1997 | Piety et al. | 250/330 |
| 5,659,538 A | 8/1997 | Stuebe et al. | 364/469.02 |
| 5,663,565 A | 9/1997 | Taylor | 250/339.11 |
| H1687 H | 10/1997 | Roe et al. | 604/485.1 |
| 6,224,699 B1 * | 5/2001 | Bett et al. | 156/64 |
| 6,408,917 B1 * | 6/2002 | Bett et al. | 156/378 |

OTHER PUBLICATIONS

Guericke W., et al. "Rolling Operation Control Circuit—Process the Infrared Camera Signals Fed During a Rolling Operation". (1 sheet) 1997.

Cincinnati Electronics Corporation, "Infrared Focal Plane Array Camera". Product Literature, (4 sheets) date unknown.

Flir Systems, "Before We Can Tell You What's Wrong, We'll Have To Take Your Temperature." Product Literature, (1 sheet) date unknown.

Information Processing, "CVIM Configurable Vision Input Module." Product Literature, (2sheets) product available from COGNEX, date unknown.

* cited by examiner

INFRARED IMAGING TO DETECT COMPONENTS ON PERSONAL CARE ARTICLES

CROSS REFERENCE TO RELATED APPLICATIONS

This application is a Continuation application claiming priority under 35 U.S.C. 120 to U.S. patent application Ser. No. 09/558,926 filed Apr. 26, 2000, U.S. Pat. No. 6,408,917 which is a Divisional application of U.S. patent application Ser. No. 09/190,692 filed Nov. 12, 1998, U.S. Pat. No. 6,224,699, which is incorporated herein by reference in its entirety.

STATEMENT REGARDING FEDERALLY SPONSORED RESEARCH OR DEVELOPMENT

Not Applicable

FIELD OF THE INVENTION

This invention relates to an improved inspection and quality level sensing system for use during processing of webs such as paper, film, composites, or the like, in dynamic continuous processing operations. More particularly, the invention relates to sensing and assessing the location and quality condition of features, characteristics, and elements characteristic of personal care articles or precursors of such articles on an article fabrication line. The invention can sense and assess, for example, the location and quality of respective components, the location and quality of ultrasonic or thermal bonding, and/or the location and amount of adhesives present in a web of personal care article precursors during the fabrication of such personal care article precursors from suitable raw material inputs.

BACKGROUND OF THE INVENTION

In assembling various elements on an e.g. endless web to make personal care articles, it is highly desirable to have a real-time inspection of various aspects of the articles being fabricated, including inspection of the articles at one or more locations on the fabrication line, as the articles are being fabricated and before fabrication is complete.

In the personal care article industry, it is known to use optical brighteners to mark components or portions of elements which form such articles in a fabrication line. When such optical brighteners are properly selected, properly applied, and properly positioned, the articles can be illuminated with ultraviolet light and/or visible light. Ultraviolet and visible light sensors can sense the optical brighteners so illuminated, and can thus record the positions, or relative positions, of components carrying such optical brighteners in such personal care articles. While some article elements can thus be detected, to applicants' knowledge, it is not known to employ such procedures to assess presence and quality of adhesive or other bonds or bonding in the context of a personal care article.

In addition, applicants are aware that some, but not necessarily all, hot melt adhesives inherently fluoresce under ultraviolet light. However, applicants are not aware of any use of such property for detecting relative positioning of elements.

In other methods of assessing or predicting product quality, structural elements such as notches, slits, slots, protrusions, depressions, or holes or the like are formed in the web of personal care articles, thus to provide a detectable structural feature which can be used to sense location of an element.

A region of magnetic discontinuity, electromagnetic discontinuity, or any combination thereof may also be used with suitable sensors of magnetic properties to show the positions of components of respective personal care articles.

The above methods of assessing or predicting product quality require modifying the personal care articles specifically for the purpose of being able to sense or detect the parameters of interest, such as for example using additional material such as an optical brightener, or a magnetic additive, or modifying the structure of the personal care articles, in order to create an element detectable by the sensors selected for the detection function. Such modifications increase the cost of personal care articles, in addition to bearing the cost of the actual detection. Further, use of such additional material, elements, or features includes the risk that the additional material, elements, or features, may be misplaced in the web, or on the respective web element, and thus give a false reading to the sensing system. There is also the risk that such modification to the product or product component may interfere with either the intended use of the personal care article or the safety of a person using the personal care article for the intended use.

It would be desired that no such additional material element, or feature, need be incorporated into or added to any element or feature of the articles being fabricated.

SUMMARY OF THE DISCLOSURE

In the invention, process heat with which the workpiece elements are inherently imbued by the process, is detected by one or more infrared sensors which sense the thermal condition inherent in a plurality of characteristics of respective features of the personal care articles being formed, and wherein the features so sensed generally have primary utility in the typical functioning of the article, and are not incorporated into the article merely to assist in the sensing operation. Characteristics which are sensed are, for example, individual components, and parts of components, of the personal care article, ultrasonic bonds, and adhesive at bonds. With proper resolution in a display of the properties so sensed, sensing such elements can pinpoint or show the exact location of such individual components, or adhesive, or ultrasonic or other thermally-formed bonds. The sensed information can be compared to stored or other reference information to determine whether or not the respective components or bonds are disposed at desired or specified locations on respective personal care articles.

The sensed information also can be compared with stored or other reference information to determine whether or not the qualities or strengths of ultrasonic bonds are effective to maintain the structural integrity of the respective personal care articles.

Further, the sensed infrared information can be compared with stored or other reference information to determine whether or not a sufficient quantity of adhesive, such as hot melt adhesive, has been applied to the personal care articles being fabricated and whether or not such adhesive has been properly distributed, in the proper relationships, on the respective components of the personal care articles.

The above comparisons can be reported to a fabrication line operator whereby the operator can monitor ongoing conformity with, or variance from, reference or other specified parameters. Variance outside specified tolerances can trigger an alarm to warn the operator that a malfunction has occurred. Further, the above comparisons can be used to cull unacceptable units of product from the personal care article fabrication line. Information from the above comparisons can also be used to shut down the processing line at certain predetermined levels of variance from specified parameters.

A significant advantage of the invention is that infrared sensors can sense the location of elements which are not readily susceptible to detection from the outside of the personal care article using sensors operating in the visible or ultraviolet wavelengths. Because of use of the infrared spectrum, the infrared system can see elements or components through one or more layers of material which are opaque to visible and/or ultraviolet light. Thus, assuming an infrared energy source, an infrared sensor can "see through" e.g. cover layers or bodyside liners of material and can display visual images of elements or components thus "seen" or detected on the interior of the personal care article. In this manner, partially or fully assembled personal care articles can be viewed or inspected for defects which may be disposed under a visually opaque element. Processing apparatus, such as a digital computer, can process the received information and compare the information with reference or otherwise known tolerances and physical values for the various components, and positions of components.

The infrared sensor typically comprises a passive infrared sensor that senses, in the personal care article work product, or work product precursor, heat that is normally inherently present in the personal care article or work product or precursor as a result of the process of assembling such work product or precursor. The heat results from, for example, ultrasonic bonding, the application of hot melt adhesive to various components of personal care articles, and residual heat otherwise developed in others of the elements as the elements are prepared for, and incorporated into, the personal care articles being fabricated on the fabrication line.

For example, certain components, such as the absorbent core, and super-absorbent therein, are inherently heated, or can be heated, to temperatures different from the temperatures of other components whereby such elements can be distinguished on the basis of temperature differences. Namely, a component can be distinguished in the visual display by controlling temperature of the component such that the component emanates infrared radiation at a rate which is unique in the web, relative to other components of the personal care article precursor.

To the inventors' knowledge, it is not known to utilize an infrared sensor to sense fibrous and/or thin-section polymeric films, fibers, or adhesives as components in a personal care article fabrication line, thereby to provide signals or information in response to the physical temperatures of components forming the personal care articles, especially where the property sensed, namely temperature, is the property inhering in the personal care article precursor in the fabrication line as a result of the manufacturing process, or manufacturing history, of the precursors. Of course, at conclusion of the manufacturing process, the personal care articles so produced continually give off heat according to temperature differentials between the personal care articles and ambient temperature, until the personal care articles reach ambient temperature. Thus, the infrared signatures of interest herein must be obtained while the personal care articles still contain discriminating amounts of such process heat.

Further to the inventors' knowledge, it is not known to use an infrared sensor to sense infrared energy and thereby to create visual images corresponding to the presence or quantity of adhesives, or strength of ultrasonic bonds, on the personal care articles. Advantageously, warm adhesives can be seen by the infrared sensor through one or more intervening visually opaque layers of material in the personal care article.

The above reading of infrared signatures can be obtained by placing suitable assemblage of infrared sensor equipment at a single sensing location in the fabrication line. Multiple images of the articles being produced on the fabrication line can, of course, be obtained by placing suitable assemblages of infrared sensor equipment at a corresponding number of locations along the fabrication line, each of such assemblages having the capability of sensing the desired information at the respective locations in the fabrication line, from which a visual image can be created, separate and distinct from the visual images developed from sensings at other locations along the fabrication line. Such multiple images, taken from corresponding multiple locations on the fabrication line, can be compared to each other as desired for assessing either or both of (a) quality of the articles being produced, and (b) the satisfactory, or not, progression of the fabrication process along the fabrication line.

A first family of embodiments of the invention contemplates fabrication apparatus for fabricating composite personal care article products, and sensing assembly quality characteristics of the personal care article products so fabricated. At least one of the components of precursors of the personal care article products so fabricated comprises a continuous web of material. The fabrication apparatus comprises fabrication machinery arranged to transport the web along a fabrication line, past a plurality of work stations where work is performed on the web, for fabricating the personal care article precursors according to a predetermined arrangement, thereby to form an array of precursors of such personal care articles on the web; separation apparatus separating the web, and the array of personal care article precursors thereon, from the web, and into individual personal care articles, including severing the web across a transverse dimension thereof; and infrared sensing and signal processing apparatus disposed in cooperating relationship with the web. The infrared sensing and signal processing apparatus senses infrared signatures of product fabricated on the web, thereby determining assembly quality characteristics of respective ones of the composite personal care articles or composite personal care article precursors, and outputting a signal representative of the sensed characteristics.

In some embodiments, the infrared sensing and signal processing apparatus comprises an infrared sensor housed in a housing physically separate and distinct from the signal processing apparatus, such that the sensor and processing apparatus are two physically separate and distinct instruments. The processing apparatus receives a signal outputted from the infrared sensor and processes such signal to provide a processor output representative of the characteristics of at least one of the personal care articles or personal care article precursors fabricated on the fabrication line.

The fabrication machinery can place an absorbent core on the web, and a bodyside liner material over the absorbent core such that the absorbent core is between the web and the bodyside liner layer, and the infrared sensing and signal processing apparatus can view and sense the position of the absorbent core through the bodyside liner material, through the web, or through any other intervening material which may be visually obstructive, such as opaque, translucent, occlusive, or the like and that is not a thermally-effective barrier to detection by a thermal sensor or other thermal detection unit.

As another expression of the invention, the bodyside liner material can have a visual printed image on a first surface thereof between the infrared sensor and an assembly quality characteristic under the respective one of the bodyside liner material and the web, the sensing by the infrared sensor sensing an assembly quality characteristic through the visual printed image.

The invention also comprehends securement apparatus such as ultrasonic bonding apparatus or adhesive bonding apparatus securing at least portions of the respective components of the personal care articles to each other to form the composite personal care article precursors in a continuous web of such precursors joined to each other along a length of the web. Thus, the invention comprehends adhesive application apparatus applying adhesive for securing at least first portions of first respective components of the personal care articles to second portions of second respective ones of the components.

In some embodiments, the infrared sensor senses the position of adhesive in such personal care articles. In addition or in the alternative, the infrared sensor senses quantities of adhesive disposed in such personal care articles.

The personal care articles can include leg elastic placement apparatus placing spaced leg elastics adjacent respective opposing outside edges of leg cut-outs of the web along the lengths of the personal care articles, and adhering the leg elastics to components of the web or on the web. Adhesive apparatus can place hot melt adhesive on the leg elastics, the infrared sensor sensing the position of the heated hot melt adhesive on the leg elastic and thus indirectly detecting the positions of the leg elastics on the personal care articles by way of the warm hot melt adhesive.

In preferred embodiments, the bodyside liner material is disposed between the infrared sensor and the leg elastics, and the infrared sensor senses the positions of the adhesive, and thus the positions of the leg elastics, through the bodyside liner material.

In some embodiments, the absorbent cores have zones comprising relative concentrations of superabsorbent, and the infrared sensor senses the zones of relative concentration of superabsorbent as distinct from the remainders of the absorbent cores.

In some embodiments, the fabrication machinery places containment flaps over the web, preferably over the bodyside liner material, as elements of the personal care article precursors. The containment flaps are secured in the web by heated hot melt adhesive or other thermal or ultrasonic bonding. The infrared sensor senses position and quantity of the heated hot melt adhesive or other thermal or ultrasonic bonding.

The securement apparatus preferably comprises an ultrasonic horn and cooperating anvil, such as an anvil roll, the ultrasonic horn providing ultrasonic energy to create bonds bonding, in the personal care article precursors, at least one component of such personal care article precursors.

The infrared sensor preferably senses the positions of the still-warm ultrasonic bonds. The output of the infrared sensor can provide an indication to an operator station when the infrared sensor does not detect the presence of the ultrasonic bonds.

Among other potential readings, the infrared sensor and signal processing apparatus can sense registration of predetermined ones of the components, either against a design location stored in memory or, relatively, against the location of a second component or other element, characteristic of the articles, e.g. an adhesive or ultrasonic bond.

The output of the infrared sensing and signal processing apparatus can send an alarm signal to an operator station identifying existence of an improper condition for at least one of the components, or can output a cull signal to cull selected ones of the personal care articles from the fabrication line, or can shut down the fabrication line, or can issue a control command, and thereby activates a registration control function.

Stated another way, the output of the infrared sensing and signal processing apparatus can call attention, in various ways, to characteristics or components of the personal care articles that are not within preselected control tolerances.

The infrared sensing and signal processing apparatus can sense the presence of leg cut-outs on the personal care articles, and control an alarm to an operator station.

Typically, the infrared sensing and signal processing apparatus senses and assesses assembly quality characteristics common to all of the personal care articles being fabricated on the fabrication line, the assembly quality characteristics, in combination, comprising a signature for the specific personal care articles being fabricated.

Preferably, the infrared sensing and signal processing apparatus has a sensitivity suitable for sensing, and thus senses, portions, or entireties, of personal care articles having temperatures as low as about 10 degrees Celsius and up to about 200 degrees Celsius.

Preferably, the infrared sensor is a single sensor or sensor array, operating in a passive mode, whereby no illuminating energy is directed toward the material being sensed. Rather, the sensor senses temperatures and differences across the overall projected surface defined by an area of one or more of the personal care articles.

Typically, the infrared sensing and signal processing apparatus comprises an infrared camera collecting infrared images from the personal care articles. Typical cameras effective to detect and distinguish infrared radiation are controlled by the electronic and optical filtering elements of the camera, or of one or more suitable camera attachments.

In preferred embodiments, the output from the infrared sensing and signal processing apparatus comprises a composite visual image representative of at least one of the personal care articles or personal care article precursors on the web. Typically, the infrared sensor comprises an infrared camera collecting, for each visual image which can be displayed, an array of infrared signals from discrete areas of the personal care articles being assessed.

The output of the infrared sensing and signal processing apparatus can represent an out-of-tolerance condition in the personal care article or personal care article precursor sensed, and wherein the infrared sensing and signal processing apparatus sends the out-of-tolerance signal to an operator station.

In preferred embodiments, the infrared sensing and signal processing apparatus comprises visual image processing apparatus.

More specifically the fabrication machinery used in fabricating personal care articles according to the invention can further comprise a first layer device and a first turning device, feeding the web into the fabrication line; an absorbent core device feeding absorbent cores to the web in the fabrication line; a second layer device and a second turning device, feeding a second outer layer into the fabrication line and over the first layer and the absorbent cover; a leg elastics device feeding leg elastics into the fabrication line; a containment flap device feeding containment flaps into the fabrication line above the second outer layer: a first bonding device applying generally continuous bonds along opposing sides of the web along substantially the entirety of the length of the web downstream from the bonding device; a second bonding device applying end seals along ends of the respective personal care article precursors; a first adhesive application device applying adhesive to the leg elastics, thereby to adhere the leg elastics in the personal care article precursors; a tape storage device feeding tapes into the fabrication line; a second adhesive application device applying adhesive to the tapes, thereby to adhere the tapes in the personal care article precursors; and a third adhesive application device applying adhesive to the containment flaps, thereby to adhere the containment flaps in the personal care article precursors over the absorbent core.

In a second family of embodiments, the invention comprehends a method of sensing assembly quality characteristics of a web of personal care articles or personal care article precursors being fabricated by processing apparatus. Each such personal care article or personal care article precursor has a bodyside liner, an outer cover, and at least one element of the personal care article or personal care article precursor disposed between the bodyside liner and the outer cover. The method comprises using infrared sensing and signal processing apparatus employing an infrared sensor, sensing assembly quality characteristics of an element, typically an element between the bodyside liner and the outer cover, through a visually relatively opaque one of the outer cover and the bodyside liner, and outputting first signals from the infrared sensor; and sending the outputted signals to an element of the infrared sensing and signal processing apparatus which can respond by outputting second signals indicative of assembly quality characteristics of the personal care articles or personal care article precursors being fabricated by the processing apparatus.

Preferred embodiments include maintaining the personal care articles free from fluorescent material, especially fluorescent materials and other additives for optical brightening as used for detection purposes, throughout the process of fabricating the personal care articles.

A third family of embodiments comprehends a method of fabricating composite personal care article products wherein at least one of the components of precursors of the personal care article products so fabricated comprises a continuous web of material, and wherein the method comprises transporting the web along a fabrication line, past a plurality of work stations where work is performed on the web, for fabricating the personal care article precursors according to a predetermined arrangement, thereby to form an array of precursors of such personal care articles on the web; separating web segments, and the array of personal care article precursors thereon, from the web, and into individual personal care articles, including severing the web across a transverse dimension thereof; and sensing infrared signatures of product fabricated on the web, thereby determining assembly quality characteristics of respective ones of the composite personal care articles or composite personal care article precursors, and outputting a signal representative of the sensed characteristics.

In a fourth family of embodiments, the invention comprehends using fabrication apparatus comprising infrared sensing apparatus disposed in cooperating relationship with the web, the infrared sensing apparatus being capable of sensing infrared properties of product being fabricated on the web, and capable of outputting signals indicative of infrared signatures of product being fabricated on the web. The fabrication apparatus also comprises visual image processing apparatus communicatively connected to the infrared sensing apparatus, and capable of accepting such outputted signals indicative of infrared signatures of product being fabricated on the web, and processing such data and thereby determining assembly quality characteristics of respective ones of the composite personal care articles or composite personal care article precursors.

In some embodiments, the signals indicative of infrared signature data outputted from the infrared sensing apparatus are in video format acceptable for processing in the visual image processing apparatus.

In preferred embodiments, the visual image processing apparatus comprises a computer module capable of comparing image data from the infrared sensing apparatus with preselected stored images.

In some embodiments, the visual image processing apparatus outputs, to an operator station display, signals indicative of visual images and derived from the infrared signatures.

The operator station display can also concurrently show respective preselected stored visual image information.

In preferred embodiments, the visual image processing apparatus compares image data for a given personal care article on the web against a predetermined data standard thereby determining conformance of the respective personal care article to the standard, and optionally outputting cull signals to cull selected ones of such compared personal care articles from the fabrication line.

In some embodiments, the visual image processing apparatus can output one or more of a fabrication line shutdown signal, a signal which calls attention to characteristics of the personal care articles not within preselected control tolerances, and a signal which activates process adjustments to adjust characteristics of the personal care articles, where such characteristics are not within preselected control tolerances before adjustment.

In a fifth family of embodiments, the invention comprehends, using visual image processing apparatus, accepting outputted signals indicative of infrared signatures of product being fabricated on the web, and processing such data and displaying the data as visual images by visual image display apparatus.

In a sixth family of embodiments, the invention comprehends a method of sensing assembly quality characteristics of a web of personal care articles or personal care article precursors being fabricated on a fabrication line by processing apparatus, wherein each personal care article or personal care article precursor has, as an element thereof, a bodyside liner, an outer cover, and at least one element of the personal care article or personal care article precursor disposed between the bodyside liner and the outer cover. The method comprises sensing infrared properties of product being fabricated on the web using infrared sensing apparatus, and outputting signals indicative of infrared properties of product being fabricated on the web to image processing apparatus. The method also comprises creating a database comprising infrared properties of product standards within selected control tolerances. Additionally, the method comprises comparing infrared properties of product being fabricated with the database data using the image processing apparatus, including a programmable logic controller capable of comparing image data from the infrared sensing apparatus with preselected stored data in the database. The method also comprises outputting processing adjustment signals from the programmable logic controller to processing apparatus of the fabrication line to effect adjustment of absorbent article processing.

In some embodiments, signals indicative of infrared properties of product being fabricated on the web are outputted in video format acceptable for processing in the visual image processing apparatus.

In some embodiments, the method includes outputting signals indicative of visual images, derived from the infrared signatures, to an operator station display using the visual image processing apparatus.

In preferred embodiments, the method includes comparing visual image data for a given personal care article on the web against a predetermined data standard and thereby determining conformance of the respective personal care article to the standard, and outputting cull or other signals to cull or otherwise manipulate selected ones of such compared personal care articles on the fabrication line.

In some embodiments, the method includes the visual image processing apparatus outputting one or more of the signals selected from the group consisting of a fabrication line shutdown signal, signal which calls attention to characteristics of the personal care articles not within preselected control tolerances, and a signal which activates process adjustments to adjust characteristics of the personal care articles, such characteristics not being within preselected control tolerances before adjustment.

BRIEF DESCRIPTION OF THE DRAWINGS

The present invention will be more fully understood and further advantages will become apparent when reference is made to the following detailed description of the invention and the drawings, in which.

Figure 1:
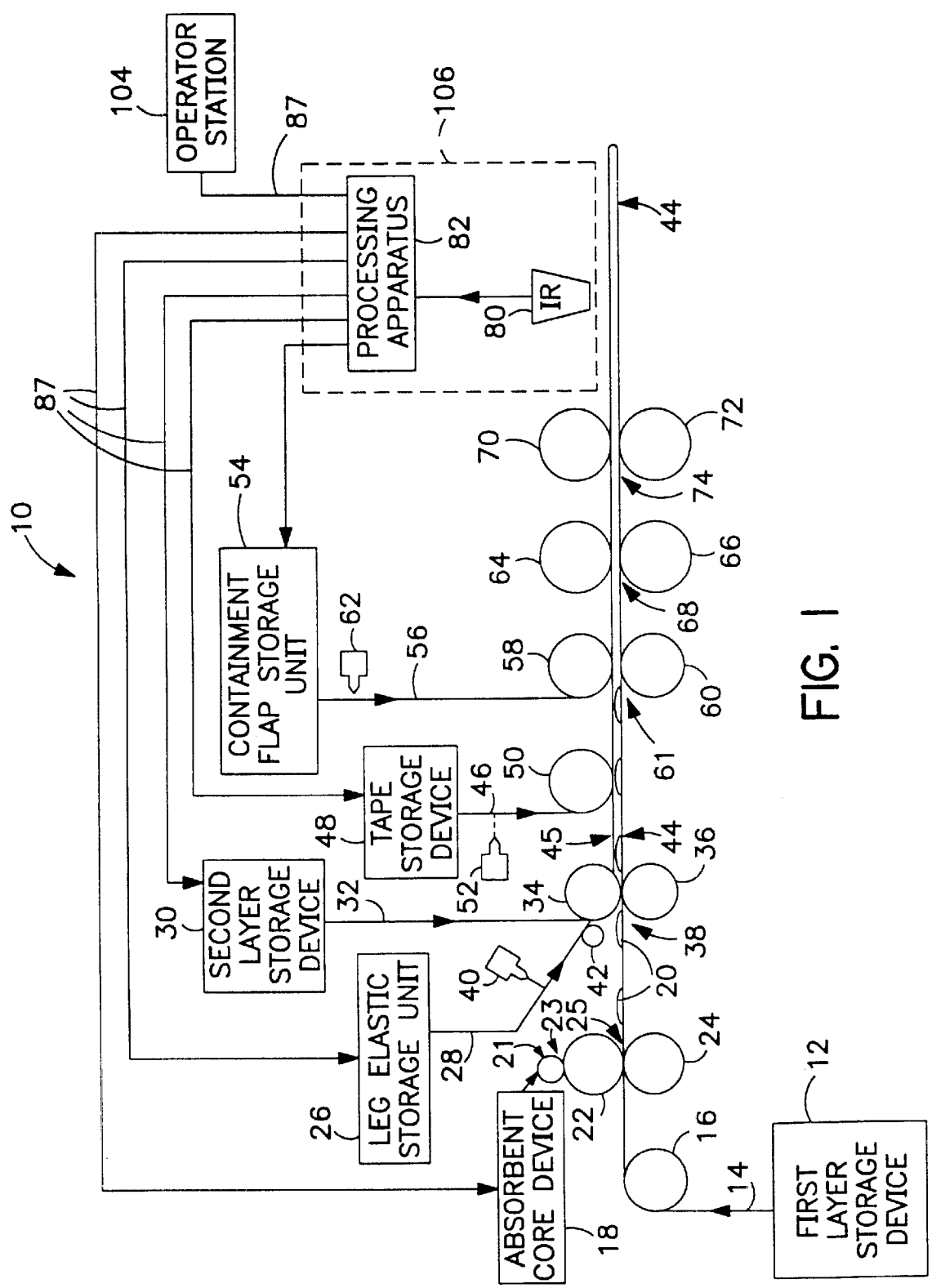
FIG. 1 is a schematic representation of a first embodiment of a fabrication line including infrared sensor and signal processing apparatus of the invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

The following detailed description is made in the context of a fabrication line for making personal care articles. Personal care articles can include, without limitation, diapers, training pants, incontinence articles, feminine care articles, and the like.

FIG. 1 illustrates a fabrication line 10 for fabricating personal care articles. Fabrication line 10 includes a first layer storage device 12 storing a generally continuous length of a first web material to be used as a first layer 14, and a turning roll 16 for turning first layer 14 into alignment along the fabrication line.

Absorbent core forming device 18 forms absorbent cores 20 for application onto first layer 14. Turning roll 21 and drive roll 22 form a first nip 23. Drive roll 22 and support roll 24 form a second nip 25. Turning roll 21, drive roll 22, and support roll 24, in combination, transfer absorbent cores 20 from absorbent core forming device 18 onto first layer 14.

Figure 5:
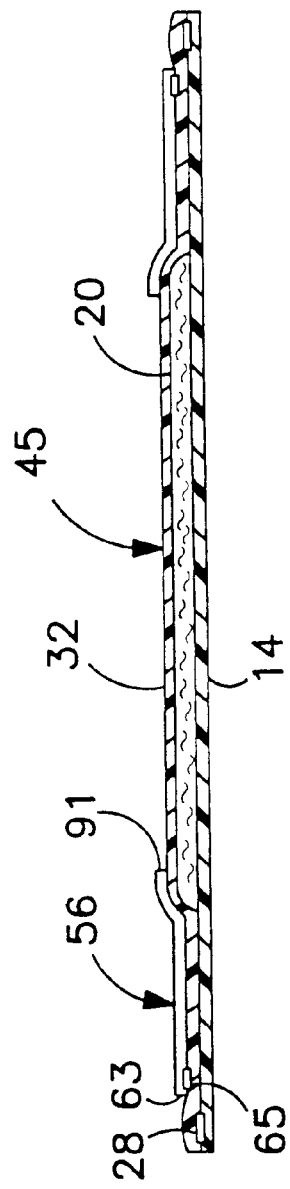
FIG. 5 is a cross-section of the underlying web, and thus of the personal care article precursor, taken at 5—5 of FIG. 2, with the leg cut-out material removed.

Leg elastics storage unit 26 stores leg elastics 28 and second layer storage device 30 stores a generally continuous length of a second web material to be used as a second layer 32, of material such as a continuous web of bodyside liner material. Drive roll 34 and support roll 36, in combination, form a third nip 38. Leg elastic adhesive application device 40 generally intermittently applies adhesive to leg elastics 28. Elastic securement roll 42, drive roll 34, and support roll 36, in combination, apply leg elastics 28, and adhesive thereon, onto second layer 32. The process preferably cuts the leg elastic at e.g. roll 34 if the adhesive is applied continuously; but may not cut the leg elastic, if the adhesive is applied intermittently, until a later step in the process, such as at product cut-off. Second layer 32 and leg elastics 28 are then joined to first layer 14 at nip 38. At nip 38, absorbent cores 20, as well as elastics 28, are disposed between first layer 14 and second layer 32 as illustrated in FIG. 5. At this stage, the above mentioned components have formed an underlying web 44 of personal care article precursors 45.

At the next stage in the fabrication line, tapes or stretch ears 46, stored in a tape storage device 48, are secured to underlying web 44 by application roll 50. Adhesive application device 52 applies adhesive to portions of tapes 46 before the tapes are applied to underlying web 44.

A containment flap storage unit 54 then applies containment flaps 56 along the full length of underlying web 44 on opposing sides of absorbent cores 20, via an application roll 58 and an opposing support roll 60 at fourth nip 61. Containment flap adhesive applicator 62 intermittently applies adhesive to containment flaps 56. The adhesive applied to containment flaps 56 is in registration with leading and trailing end portions of the personal care article precursors 45 on underlying web 44, such that the adhesive secures the full widths of containment flaps 56 in web 44 at front and back waist portions of personal care article precursors 45 and secures only outward edge portions of containment flaps 56 in web 44 along the intervening mid-portions (crotch portions) of the personal care articles.

Figure 2:
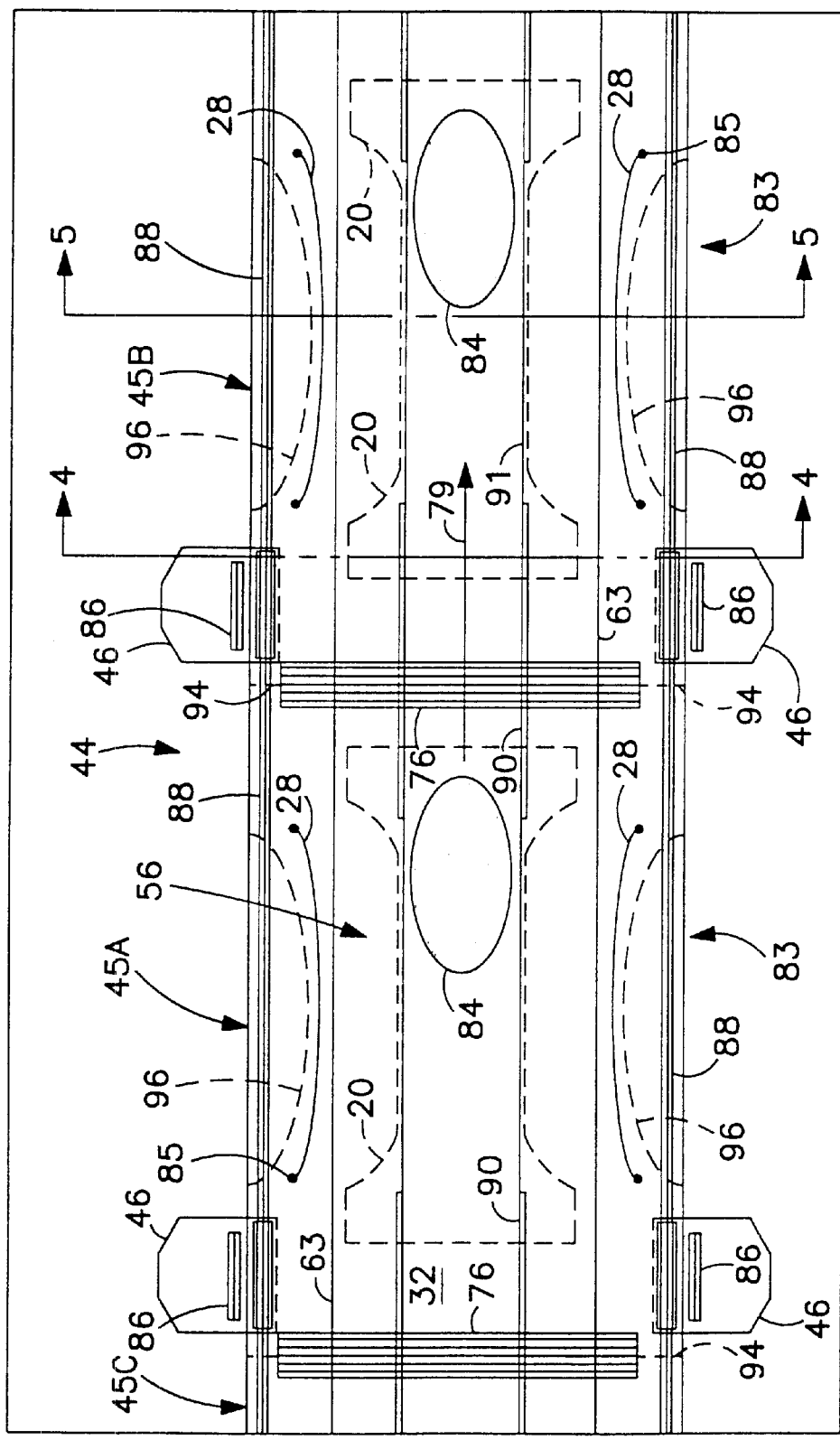
FIG. 2 is a line drawing representative of a top view of an image of an underlying web moving along the fabrication line, and as viewed by the infrared sensor.
Figure 4:
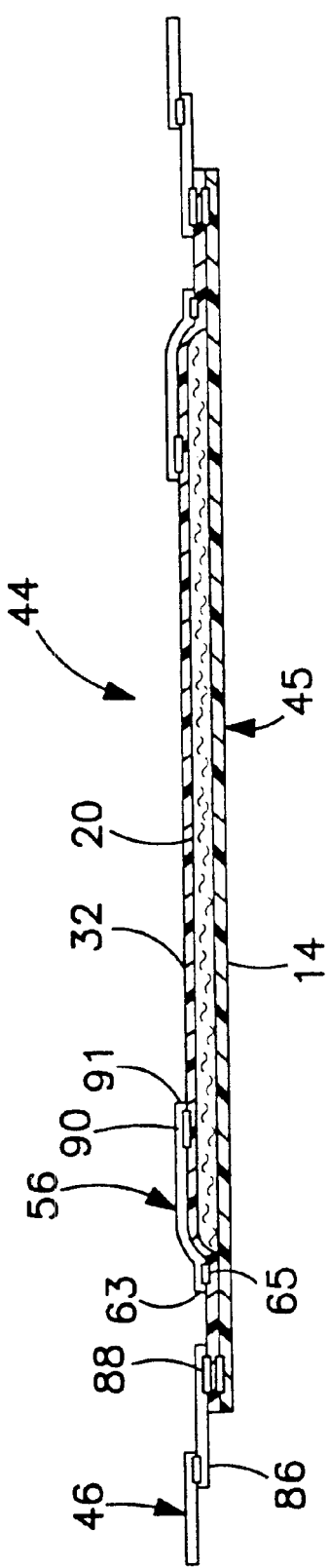
FIG. 4 is a cross-section of the underlying web, and thus of the personal care article precursor, taken at 4—4 of FIG. 2.

Thus, as illustrated in FIGS. 2, 4, and 5, outer edges 63 of containment flaps 56 are secured in web 44 along the entire length of a given personal care article precursor by a generally continuous bond 65. Correspondingly, inner edge 91 is bonded in underlying web 44 only at front and back portions of the personal care article precursors (FIGS. 2, 4), whereby the intermediate portion of the article precursor, namely across crotch portion 83, is not bonded to any underlying web element. Accordingly, when containment flaps 56 are relaxed, inner edges 91 can stand up along the mid-portion, namely crotch portion 83, while remaining secured at bond 65 to materials of underlying web 44.

Underlying web 44, including tapes 46, containment flaps 56, and leg elastics 28, then advances to ultrasonic horns 64 and supporting anvil roll or rolls 66. Ultrasonic horns 64 and anvil rolls 66 form a fifth nip 68 where outward portions of multiple components of underlying web 44 are ultrasonically bonded to each other. In this manner, first and second parallel lines of ultrasonic bonding 88 are formed generally along the entirety of the length of underlying web 44, bonding first layer 14 and second layer 32 to each other along substantially the entire lengths of the respective webs downstream of nip 68. First layer 14 and second layer 32 are preferably co-extensive along the entire length, and across the entirety of the width, of underlying web 44, including between the first and second lines of ultrasonic bonding.

Underlying web 44 then advances to end seal ultrasonic horn 70. End seal ultrasonic horn 70, in cooperation with anvil roll 72, forms a sixth nip 74. At nip 74, ultrasonic horn 70 forms intermittent end seals 76 across portions of underlying web 44 corresponding to, and bridging, the leading and trailing end portions of succeeding ones of the respective personal care article precursors.

At this point in the process, underlying web 44 has been substantially transformed into a series array of personal care article precursors, joined to each other at end seals 76, which later in the process form the respective leading and trailing edges of the resulting personal care articles. The major remaining steps comprise farming leg cut-outs to fit the personal care article about the legs of a wearer, and severing across underlying web 44 to thus form the leading and trailing edges of the above-mentioned leading the trailing end portions of individual personal care articles, and thereby to separate individual personal care articles, including individual web segments, from the generally continuous web.

In this embodiment, underlying web 44 next advances past infrared sensor 80. Infrared sensor 80 preferably comprises a passive Infrared sensor sensing infrared radiation emanating from discrete areas of the personal care articles being assessed. Sensor readings are thus taken from various positions across underlying web 44 and along a pre-defined length of the web. Namely, sensor 80 senses individual radiation rates at closely spaced locations across the full width of the web, thus to provide an array of readings representing a comparative temperature profile across the width, and along a specified portion of the length of the web infrared sensor 80 does not retain, record or report visible light, or ultralight received from the underlying web.

Figure 7:
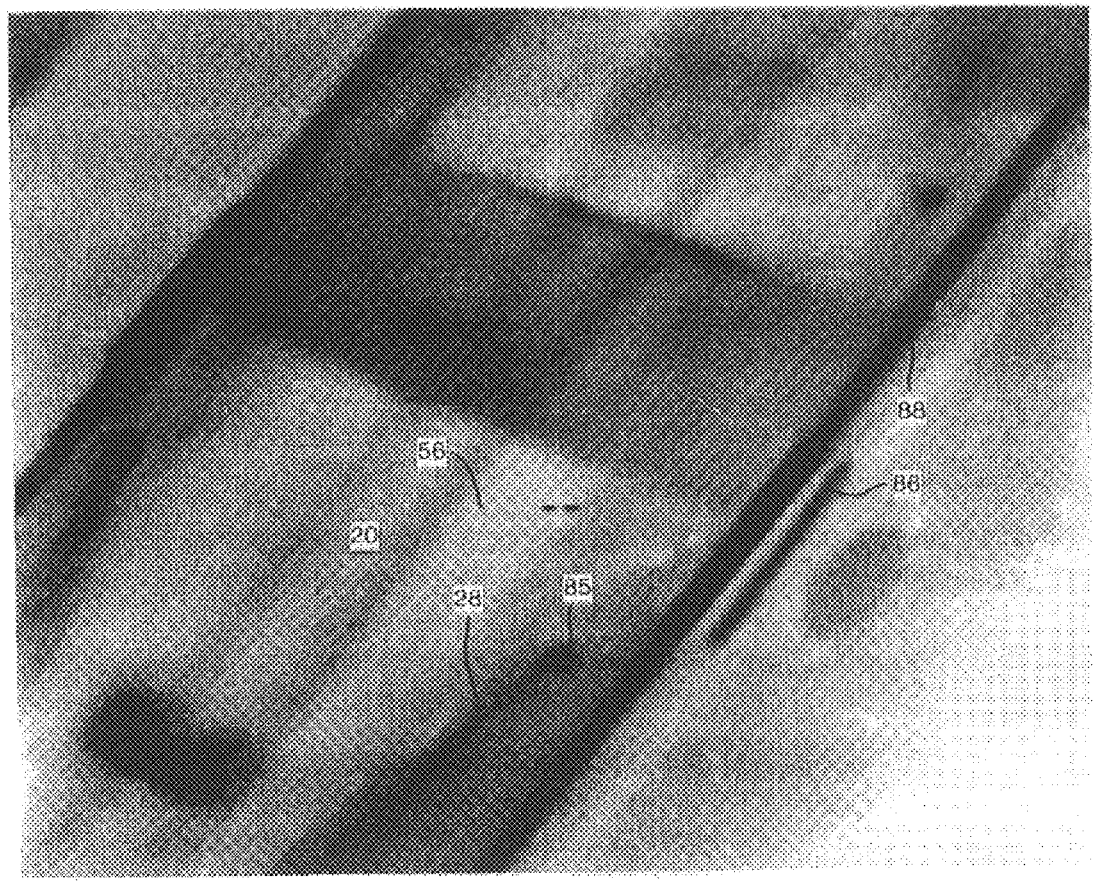
FIGS. 7 and 8 are pictorial representations of actual visual images created and used in sensing assembly quality according to the invention.
Figure 8:
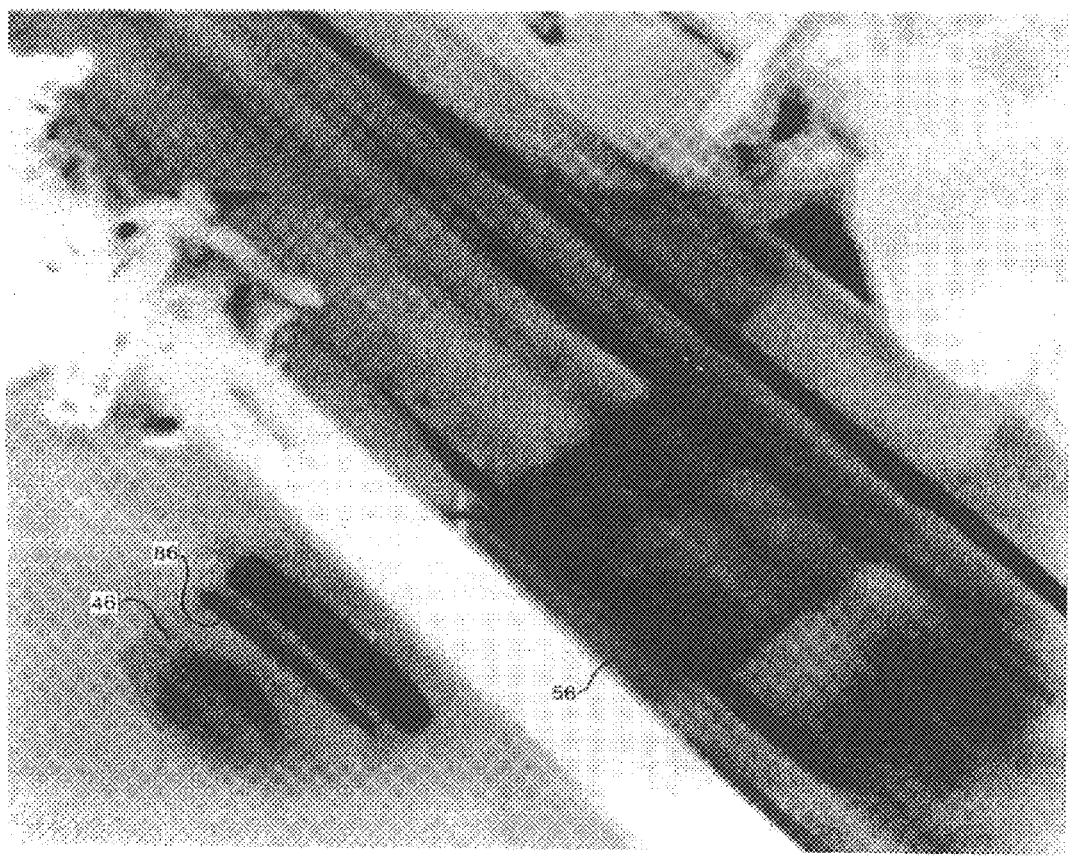

Sensor 80, optionally in combination with signal processing apparatus 82, converts the individual radiation readings sensed along the length and width of the web into a composite visual image representing the width, and the specified portion of the length, of the web on a visual display screen, such as a computer monitor or the like, illustrated by outline 81 in FIG. 2. FIG. 2 is a line drawing representation of the visual image so displayed, showing a top view of a section of underlying web 44, on the monitor. The image shown includes a first full personal care article precursor 45A, a major portion of a second precursor 45B, and a minor portion of a third precursor 45C. FIGS. 7 and 8 are reproductions of actual visual images produced according to the invention, showing fabrication of personal care articles in a continuous web process, and illustrating visibility of elements such as leg elastic which are hidden from visual observation by the overlying cover layer 32.

The different temperatures, or otherwise stated the different rates of emanating infrared energy from the several elements of web 44, and thus precursors 15, create respective different shades of gray in the visual image displayed (FIGS. 7, 8), or of color on a color image display, whereby at least the outlines of the respective elements are clearly distinguished from each other in the displayed visual image.

For example, in this embodiment, FIG. 2 illustrates at arrow 79 the direction of advance of web 44, and shows absorbent cores 20. While absorbent cores 20 are illustrated in dashed outline in FIG. 2, the outline of the cores can be clearly displayed as part of the visual image created from the sensing of infrared energy, even though second layer 32 overlies the entirety of the respective absorbent cores and thus blocks visual detection of the outer edges of the absorbent cores. Absorbent cores 20 are readily detected by infrared sensor 80 because absorbent cores 20 typically have a different temperature than either first layer 14 or second layer 32.

Such image of absorbent cores 20 and other elements of underlying web 44 is utilized by sensor 80 and/or processing apparatus 82 to define a signature for the products being fabricated, including a signature for e.g. absorbent cores 20 relative to the rest of the elements of underlying web 44. Such a signature can be defined as a distance, from a side edge running along a portion of the length of the absorbent core, e.g. to an edge of underlying web 44, to an edge of first layer 14, or to an edge of second layer 32. Such distance can be compared to tolerance values (distances) in a predetermined or preselected range which determine positioning of the several elements of web 44 relative to each other.

The signature can also be defined in terms of the absolute temperature, for example the amount of infrared radiation being received, from the article being sensed, thus to monitor and control the absolute temperature of one or more of the elements being sensed, thus to detect overheating, or excessively cool, conditions.

If one or more of the positions of respective absorbent cores 20, or other elements, with respect to other elements of underlying web 44, are out of the preselected range, processing apparatus 82 can send a control signal to the respective element placement devices, such as absorbent core device 18 and/or drive roll 22 to adjust the positioning of e.g. the absorbent cores at first layer 14. Positioning of other elements can be similarly adjusted.

Signal processing apparatus 82 can, in addition or in the alternative, provide an audible or visual warning, to an operator station 104, and thus to a fabrication line operator, that e.g. absorbent cores 20 are not being placed at proper positions on first layer 14.

A second preselected range greater than the first preselected range can also be utilized for providing a second type of response to the condition sensed. For example, if absorbent cores 20 are out of position from other components by the distance set forth in the second preselected range, individual units of product can be culled either by the operator or by command of signal processing apparatus 82, or fabrication line can be shut down and production discontinued until repairs or adjustments are made.

Signal processing apparatus 82 preferably includes a computer controller such that preselected ranges for the distances between ones of the elements can be monitored. For example, a distance between an edge of absorbent core 20 and a second component of the web, such as an outer edge of the web along the length of first layer 14 or second layer 32, can be monitored, and changed or adjusted as necessary according to parameters set up in processing apparatus 82 or elsewhere in apparatus of the invention.

FIG. 2 illustrates superabsorbent zones 84 where superabsorbent material has been incorporated into cores 20. Superabsorbent material is typically used in particle form. The particles are typically heated and thus thoroughly dried, before being incorporated into core 20, and thence into web 44. Absorbent core device 18 (or other corresponding apparatus of known design) is conventionally configured to add the heated superabsorbent particles to one or more selected portions of the absorbent cores used in fabrication line 10.

Such superabsorbent, being heat dried immediately prior to use, has a temperature greater than the temperature of absorbent core 20 in general, and greater than the temperature at other adjacent portions of underlying web 44. Therefore, images of superabsorbent zones 84 where superabsorbent material has been incorporated into the core can be distinguished on the visual display from the core in general. Thus, the detected locations of superabsorbent zones 84, and the intensity of the signals sensed, can be compared to preselected or predetermined zones and intensities, by processing apparatus 82. Processing apparatus 82 can then send control signals to absorbent core device 18 to control the amount and location, of placement of superabsorbent in subsequently fabricated absorbent cores 20.

Processing apparatus 82 can provide an operator with a visual display and/or a warning signal, and/or can make process condition adjustments and/or can shut down fabrication line 10 as described earlier with respect to absorbent cores 20 upon any detection of an out-of-tolerance condition, by issuing suitable commands through feedback lines 87.

FIGS. 2 and 7 illustrate leg elastics 28 in underlying web 44. In the embodiment illustrated, stretched leg elastic material is fed as continuous strands from storage unit 26. Adhesive is applied along the leg elastic material. Leg elastics 28 are then incorporated into web 44, and secured to second layer of the personal care article precursors being formed along underlying web 44. As described earlier with respect to absorbent cores 20, infrared sensor 80 can sense the difference between the temperature of leg elastics 28 and adjacent elements, and in some cases can distinguish the adhesive, with respect to the temperatures of other adjacent elements of web 44. Infrared sensor 80 can provide such sensing even though one of first layer 14 and second layer 32 is positioned between leg elastics 28 and the infrared sensor.

By processing the data received by sensor 80, sensor 80 and/or processing apparatus 82 can establish an image signature representative of the actual locations and sizes of elements of leg elastics 28, and can compare the actual and relative locations and sizes of such leg elastic elements to preselected stored values associated with such locations and sizes. As noted earlier with respect to absorbent core 20, processing apparatus 82 can send control signals to leg elastic storage unit 26 and/or adhesive application device 40 to adjust the positioning of leg elastics 28, or the amount or timing of intermittent application of hot melt adhesive to the leg elastics. In addition, or in the alternative, sensor 80 and/or processing apparatus 82 can provide an operator with a visual display of the image signature and/or can provide a warning signal, or can shut down fabrication line 10 in response to the absence or misplacement, or poor bonding, or another improper condition, of leg elastics 28.

Tapes 46, also known as stretch ears, generally comprise two or more layers of material. If the multiple layers have not been previously joined, adhesive application device 52 can apply adhesive to form or secure the layers to each other, thus completing formation of tapes 46, and can apply adhesive for at least temporarily securing such tapes in web 44. Pairs of tapes 46 can be intermittently applied to underlying web 44 at spaced locations on opposing sides of personal care article precursors 45 as shown in FIGS. 1 and 2. Tape application roll 50, or other apparatus (not shown) can comprise an intermittent motion or variable speed device that periodically places discrete tapes on web 44 at the appropriate spaced locations.

Adhesive, preferably comprising a hot melt adhesive, applied by adhesive application device 52, forms intermittent tape bonds 86, shown in FIGS. 2, 7, and 8, securing tape components to each other or securing layers of tape material to each other.

Likewise, containment flaps 56 can be positioned by application roll 58 along the entire length of underlying web 44 adjacent opposing sides of absorbent cores 20 as shown in FIGS. 2, 7, and 8.

Ultrasonic horn 64 and supporting anvil roll 66, in combination, continuously form continuous ultrasonic structural bonds 88, bonding first layer 14 and second layer 32 to each other along opposing sides of underlying web 44 as illustrated in FIGS. 2 and 7. Structural bonds 88 are preferably continuous along the length of web 44. By "continuous," we include bonds which comprise a generally continuous array of separate and distinct, discreet bond elements, such as an array of dots spaced from each other in an array. Ultrasonic horn 64 also preferably forms ultrasonic bonds between tapes 46 and underlying web 44 at spaced locations along the length of web 44 where tapes 46 are incorporated into the web, and thus along the lengths of bonds 88. Such bonds, as well as bonds 88, can be formed by any known bonding technique, such as, without limitation, ultrasonic bonding, adhesive bonding, or thermal bonding.

An adhesive applicator generally illustrated at 64, in combination with anvil roll 66, or other suitable apparatus, can also intermittently apply adhesive, and thus is, bond inwardly-disposed edges 91 of containment flaps 56 to second layer 32 as at bonds 90. Such containment flap bonds 90 are positioned at areas, along underlying web 44, which correspond to the front and rear portions of personal care article precursors 45 being formed, as illustrated in FIG. 2. Bonds 90 can, in the alternative, be fabricated by suitable application of adhesive by application device 62.

Figure 6:
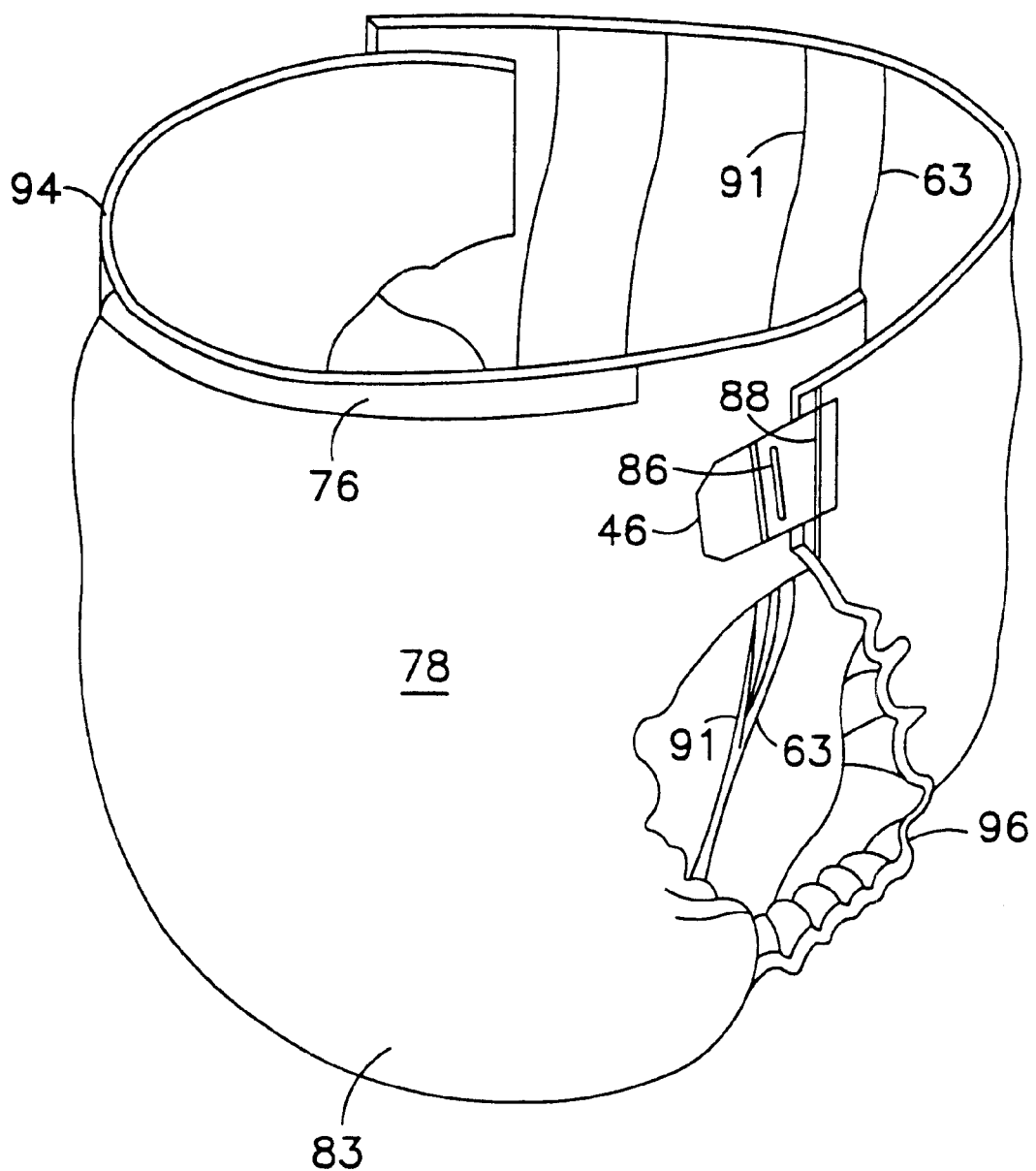
FIG. 6 shows a pictorial view of a personal care article made according to the invention.

With bonds 90 being formed only at the front and rear portions of the personal care article precursors, edges 91 are not bonded to layer 32 at the crotch portions of personal care article precursors 45. Accordingly, containment flaps 56 can stand up, with edges 91 disposed away from layer 32 when the resulting, separated, personal care article is mounted on, thus to interface with the body of the wearer, and to deter leakage of exudates outwardly beyond containment flaps 56. FIG. 6. A conventional containment flap elastic (not shown) generally extends along the length of inwardly disposed edge 91 of containment flap 56 to assist in erecting, or standing up, the containment flap against the body of the wearer, thus providing a seal element against the body of the wearer.

While FIG. 1 shows a single ultrasonic horn 64 and single anvil roll 66 bonding containment flaps 56 and tapes 46, such bonding can be done by multiple ultrasonic horns (not shown) and/or multiple anvils. For example, multiple ultrasonic horns can be spaced along the length of web 44 to form multiple bonds 86, 88, and 90 on opposing sides of web 44 and/or elsewhere as desired. Ultrasonic horns separate and distinct from the horn illustrated at 64 can separately bond tapes 46 to underlying web 44.

From nip 68, web 44 then travels to nip 74 formed by end seal ultrasonic horn 70 and anvil roll 72. End seal ultrasonic horn 70, in combination with anvil roll 72, intermittently forms end seal bonds 76 across a major portion of the width of underlying web 44 by bonding first layer 14 and second layer 32 in the web, and preferably to each other. During further processing of web 44 (not shown), the web is completely severed across its width whereby segments of the web defining individual personal care article precursors 45 are completely severed from the web and are thus formed into individual personal care articles 78. The line of such severance is indicated at 94 in FIG. 2, intermediate the leading and trailing edges of end seal bonds 76. Thus each end seal bond 76 is divided by such severance into two parts. A first part of bond 76 seals a rear waist of a leading personal care article precursor (e.g. 45B) and a second part of bond 76 seals a front waist of a respective trailing personal care article precursor (e.g. 45A).

In a step prior to severing web 44, leg cut-outs 96 are removed from underlying web by a cutting roll (not shown) or the like and removal suction. Leg cut-outs 96 are illustrated by dashed lines at the crotch portions 83 of personal care article precursors 45A, 45B in FIG. 2. Such leg cut-outs generally are made before web 44 is severed into individual personal care articles 78.

Figure 3:
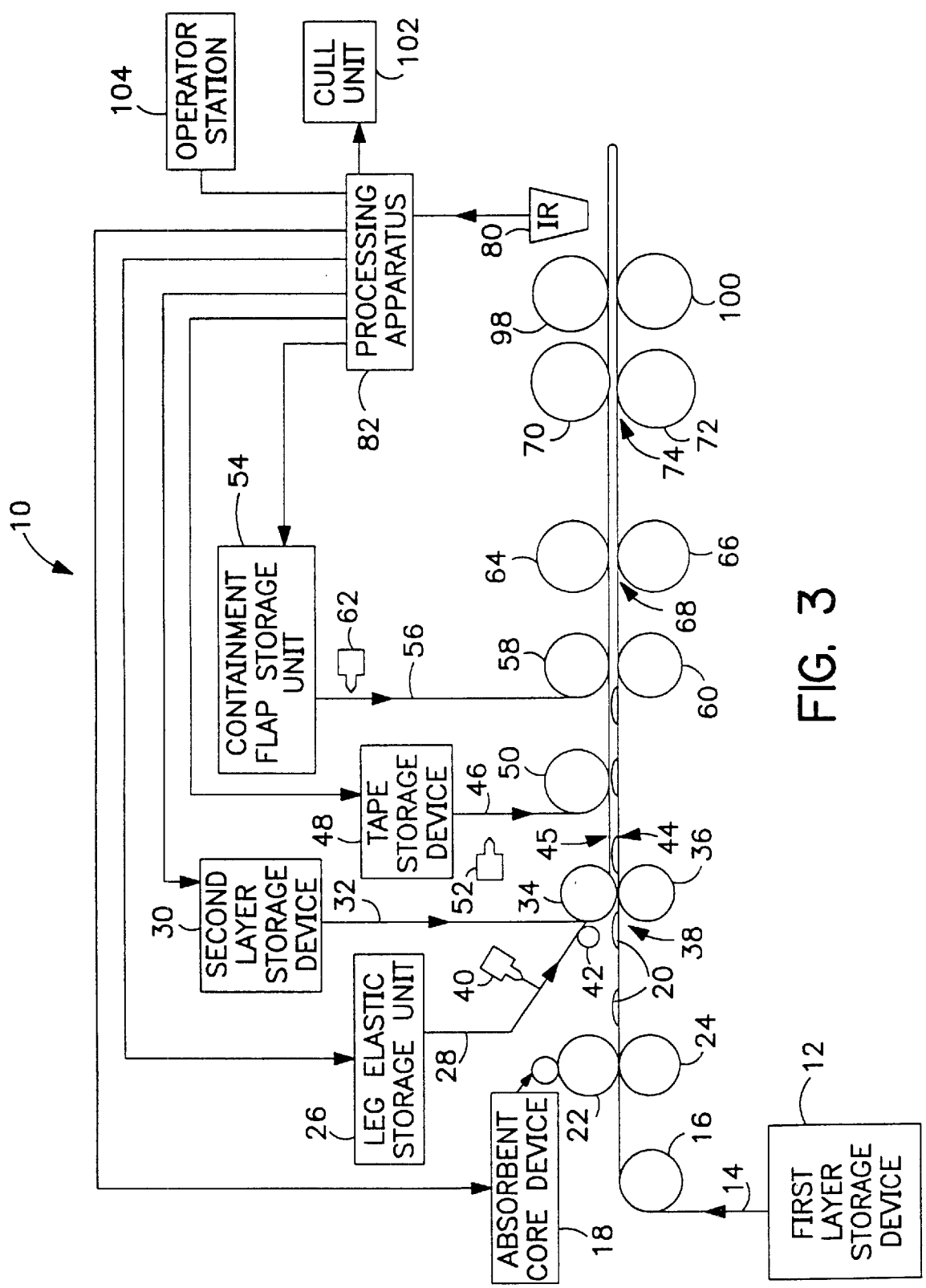
FIG. 3 is a schematic representation of a second embodiment of a fabrication line, including infrared sensor and signal processing apparatus of the invention.

In another embodiment, shown in FIG. 3, infrared sensor 80 senses underlying web 44 after leg cut-out cutting device 98, working against opposing roll 100, has cut leg cut-outs 96 and the waste material has been removed from web 44. This embodiment generally operates in the same manner as the embodiment of FIG. 1. However, processing apparatus 82, using an image developed from data collected by infrared sensor 80, can sense the presence, or absence, of ultrasonic bonds 88 in zones corresponding to leg cut-outs 96. If such bonds 88 are present in the crotch portion of precursors 45, processing apparatus 82 concludes that the leg cut-outs have not been successfully removed, and the severed personal care article is culled and an adjustment command is sent to suitable elements of the fabrication machinery. If the condition persists, fabrication line 10 can be shut down by processing apparatus 82. Further, the operator can be warned of the failure of leg cut-out cutting device 98 whereby he or she can personally intervene to assure that appropriate corrective action is taken.

First layer storage device 12 preferably comprises a progressively wound roll of material corresponding to first layer 14. Storage device 12 generally is designed to accommodate change-over rolls so that when a first roll of layer 14 material is exhausted, the leading end of a second roll can be automatically fed along with the trailing end of the first roll, so that feeding of first layer 14 can be changed over from the first roll as feed roll to the second roll as feed roll while continuously feeding layer 14 material to fabrication line 10.

First layer 14 can comprise an outer cover of the personal care article. First layer 14 can be formed from a single layer, or from multiple components, layers, or partial layers, of material, typically in surface-to-surface relationship with each other, such that the resulting outer cover is substantially impermeable to liquids. A typical first layer 14 can be manufactured from a thin plastic film or other flexible liquid-impermeable material. For example, first layer 14 can be formed from a polyethylene film having a thickness of from about 0.012 millimeter to about 0.051 millimeter.

When it is desirable that first layer 14 have a more cloth like feeling, layer 14 can comprise, for example, a polyethylene film laminated to a nonwoven web, such as a spunbonded web of polyolefin fibers. For example, a polyethylene film having a thickness of about 0.015 millimeter can have thermally or otherwise laminated thereto a spunbonded web of polyolefin fibers having a thickness from 1.5 to 2.5 denier per filament, which nonwoven web has a basis weight of about 24 grams per square meter. Further, first layer 14 can be formed of a woven or nonwoven fibrous web which has been totally or partially constructed and/or treated to impart a desired level of liquid impermeability to selected regions that are adjacent or proximate absorbent core 20 Still further, first layer 14 can optionally be composed of a micro-porous material which permits vapors to escape from absorbent core 20 and through first layer 14 while preventing liquid exudates from passing through the first layer.

Absorbent core device 18 can comprise conventional apparatus which forms absorbent cores that are positioned on first layer 14 by drive roll 22. Such absorbent core forming devices are well known in the personal care art.

Absorbent cores 20 suitably comprise a relatively thicker structure, compared to first layer 14 or second layer 32, and include a matrix of hydrophilic fibers, such as a web of cellulosic fluff, preferably in combination with a high-absorbency material commonly known as superabsorbent material. In a particular embodiment, absorbent cores comprise a mixture of superabsorbent hydrogel-forming particles and wood pulp fluff. In place of the wood pulp fluff, one can use synthetic, polymeric, meltblown fibers or a combination of meltblown fibers and natural fibers. The superabsorbent can be substantially homogeneously mixed with the hydrophilic fibers or can be otherwise combined into the absorbent core to form superabsorbent zones 84 having relatively higher concentrations of superabsorbent particles. Other configurations of superabsorbent are also contemplated, but use of superabsorbent zones 84 generally can provide for the best containment of body exudate fluids.

Alternatively, an absorbent core 20 may comprise a laminate of fibrous webs and superabsorbent material or other suitable means of maintaining a superabsorbent material in a localized area.

Absorbent cores 20 can have any of a number of overall shapes. For example, the absorbent core can be rectangular, oval-shaped or the modified hour glass shape shown in FIG. 2. The relatively thicker structure of absorbent core 20 generally does not extend over the entire dimensions of first layer 14 or second layer 32.

The superabsorbent material in absorbent core 20 can be selected from among natural, synthetic and/or modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable by aqueous fluid, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Drive roll 22 can comprise a conventional absorbent-transferring roll for receiving and transferring absorbent cores 20 to first layer 14.

Leg elastics storage unit 26 can comprise a conventional elastics unit applying first and second spaced elastics onto second layer 32 via elastic securement roll 42.

Leg elastics 28 typically are pre-stretched before application to second layer 32. Materials suitable for forming leg elastics 28 include strands, ribbons, or one or more layers of a polymeric and/or elastomeric material. Leg elastics 28 can suitably comprise one or more individual strands of elastomeric material. For example, a plurality of elastic strands can be configured in a spatially separated, generally parallel arrangement. A suitable elastic strand can, for example, be composed of a 470 decitex LYCRA® elastomer, 620 decitex LYCRA® elastomer or other elastomers having suitable characteristics.

In other embodiments, leg elastics 28 can be intermittently applied in the crotch portion of completed, and individually defined and separated personal care articles 78.

In most embodiments rear waist elastics (not shown) are contemplated near end seal bonds 76 to enable the finished personal care articles 78 to conform to and fit the body of any wearer having a waist size within a specified range of sizes. Such rear waist elastics can comprise strands, ribbons, or one or more layers of a polymeric and/or elastomeric material, preferably a material which can be adhered to personal care article 78 while the elastics are in a stretched condition. Rear waist elastics can comprise one or more individual strands of elastomeric material, preferably in a spatially separated, generally parallel arrangement. While rear waist elastics can be made of materials similar to leg elastics 28, the amount of retractive force, and generally the thickness of the respective elastic strands, or like material, is generally less.

Second layer storage device 30 preferably comprises a progressively wound roll of material corresponding to second layer 32. Such device 30 generally is designed to accommodate changeover rolls so that when a first roll of layer 32 material is exhausted, the leading end of a second roll can be automatically fed along with the trailing end of the first roll, so that feeding of second layer 32 can be changed over from the first roll as feed roll to the second roll as feed roll while continuously feeding layer 32 material to fabrication line 10.

Second layer 32 can comprise a bodyside liner in the finished personal care article. A suitable second layer 32 acting as a bodyside liner can be manufactured from a wide selection of web materials, such as porous foams, reticulated foams, apertured plastic films or natural or synthetic fibers. For example, second layer 32 can comprise wood or cotton fibers. Other possible materials are synthetic fibers, such as polyester or polypropylene fibers, or a combination of natural and synthetic fibers. Second layer 32 can beneficially be utilized to help isolate the aqueous body exudate liquids, which are held in absorbent core 22, from the skin of the wearer.

In addition, various woven and nonwoven fabrics can be used for the bodyside liner. For example, the bodyside liner can be composed of a meltblown or spunbonded web of polyolefin fibers. The bodyside liner can comprise a carded and/or bonded web composed of natural and/or synthetic fibers. The bodyside liner can comprise a substantially hydrophobic material wherein the hydrophobic material is treated with a surfactant or otherwise processed to impart a desired level of wettability and hydrophilicity. In a particular embodiment of the present invention, the bodyside liner can comprise a spunbonded polypropylene fabric composed of about 1.0–3.2 denier fibers formed into a web having a basis weight of about 22 grams per square meter and a density of about 0.06 grams per cubic centimeter. Such fabric is treated with about 0.3 weight percent of a surfactant.

Second layer 32 can comprise a bodyside liner having a multiplicity of components, layers, or partial layers, which correspond to any of the materials disclosed herein, as well as others known in the art. The bodyside liner can also comprise a plurality of the above mentioned materials in surface-to-surface relationship with each other.

In other embodiments, second layer 32 can comprise an outer cover and first layer 14 can comprise a bodyside liner. Such a reversal of webs requires corresponding changes in the layout of fabrication line 10 in order to arrive at the same ultimate arrangement of elements.

Tape storage device 48 and application roll 50 can comprise conventional elements known for positioning tapes 46 on an underlying web such as web 44. While FIG. 1 illustrates tapes 46 being positioned on an upper surface of second layer 32, namely an outer surface of the personal care articles, in other embodiments, the tapes can be positioned between the first and second layers, or on an outer/lower surface of the first layer/outer cover.

Tapes 46 can comprehend stretch ears and can comprise any of a variety of fastening elements. For instance, tapes 46 can comprise hook and loop fastener elements for securing a rear portion of personal care article 78 to a front portion of the personal care article, in well known manner. Other well known securing elements can be used to support personal care article 78 on the wearer. For example, a cohesive system, an adhesive fastener system, or the like can be utilized as securing elements, with suitable cooperating elements on the front portion of the personal care article, as necessary, to support personal care article 78 on the wearer.

Containment flap storage unit 54, in combination with containment flap application roll 58 and support roll 60, can comprise a containment flap application system. Such a system can continuously apply containment flap material along opposing sides of absorbent core 20, continuously sealing the outer edges of the containment flaps to web 44 at second layer 32, and intermittently sealing the inner edge 91 so that the containment flaps are free to stand up at inner edges 91 only at crotch portions 83 of personal care articles 78. Containment flaps 56 can be made in whole or in part of materials set forth for second layer 32. However, to prevent leakage of exudates transversely past the containment flaps, containment flaps 56 are preferably formed from liquid impermeable materials set forth for first layer 14. Containment flaps 56 can comprise multiple layers of material. In such an arrangement, some layers can be impermeable and others permeable, to body exudate liquids.

Ultrasonic horns 64, 70 preferably comprise well known rotary ultrasonic horns such as the horns set forth in U.S. Pat. No. 5,110,403 to Ehlert issued May 5, 1992, the disclosure of which is hereby incorporated by reference in its entirety.

Adhesives applied by adhesive application devices 40, 52, 62 generally comprise hot melt adhesives which are sufficiently hot to be fluid when applied, and which solidify as they transfer heat to the ambient environment and thereby cool down. The heat radiated from such elevated temperature adhesives is detectable by infrared sensor 80 even if the adhesives are covered by other elements of underlying web 44 whereby the adhesives are hidden from visual view. Thus, the positions and quantities of the several warm adhesives can in general be sensed by infrared sensor 80 through other components of personal care articles 78.

Personal care articles 78 typically comprise absorbent articles suitable for absorbing and retaining body exudates. Such articles include, without limitation, disposable diapers, training pants, feminine care articles, and adult incontinence products.

Infrared sensor 80 preferably comprises a passive infrared sensor sensing differences in temperature at positions along underlying web 44 as the web moves along fabrication line 10. Namely, sensor 80 does not normally rely on projecting any energy at underlying web 44 for the purpose of enhancing the ability to sense respective elements of the web.

However, while not the preferred embodiment, the invention does contemplate that one or more of the elements to be detected can be heated, or cooled, specifically for the purpose of enhancing its detection, to a temperature which will enhance the viewer's ability to distinguish the respective element or elements in the visual image display.

Infrared sensor 80 does not record or retain visible light or ultraviolet light from the underlying web. Infrared sensor 80 does not sense fluorescent material applied to the web. Specifically, preferred embodiments of this invention contemplate personal care articles 78 being free from any (e.g. fluorescent) material applied for the purpose of being detected as representative of the presence and positioning of one or more elements of personal care article precursors 45 on processing line 10.

On the other hand, this invention does comprehend creating a single composite visual image from signals received from a combination of sensors comprising an infrared sensor and one or both of a visual sensor and an ultraviolet sensor. In the case of using visual or ultraviolet sensors in combination with infrared sensor 80, any e.g. visual or fluorescent material known to be coated/painted onto an article to be detected, for the purpose of enhancing detection, can also be used in this invention for assisting detection by the respective visual or ultraviolet sensor.

Infrared sensor 80 generally comprises an infrared vision camera. Examples of suitable cameras are e.g. Model 575 from AGEMA Infrared Systems AB, Danderyd, Sweden, and INFRAMETRICS SC1000 Therma CAM by INFRAMETRICS, INC. of North Billerica, Mass.

Any apparatus used as sensor 80, optionally in combination with processing apparatus 82, should have suitable discrimination capability to suitably define the outlines of the several elements of web 44 in the visual image. Accordingly, sensor 80, or a combination of suitable sensors, and processing apparatus 82 as appropriate should be able to distinguish elements of at least 0.5 mm in size, and to detect the locations of component edges to a resolution of not less than 0.5 mm, thereby to provide a clear infrared signature indicating the relative locations of the respective elements on web 44.

Infrared energy suitable for being sensed according to the invention, by sensor 80, is defined as having a wavelength or frequency of about 1 micron to about 15 microns, preferably about 3 microns to about 12 microns.

Ranges of temperatures which can be sensed by the above exemplary apparatus are on the order of about −10 degrees Celsius to about 1500 degrees Celsius above ambient. Certainly lower temperatures, or higher temperatures, can be sensed by selecting infrared sensing apparatus designed for the respective higher or lower temperatures. However, in general, the invention is practiced sensing temperatures in the range of about 10 degrees Celsius to about 200 degrees Celsius, preferably about 15 degrees Celsius to about 100 degrees Celsius.

Assuming normal camera and processor sensitivity of the above equipment as offered by the above suppliers, temperature differentials between different elements of web 44 which can be detected, whereby the respective edges of the respective elements can be seen on the visual display, can be as small as about 0.1 degrees C. to about 10 degrees C., preferably no more than about 0.2 degrees C. to about 5 degrees C. Smaller temperature differentials can be detected by providing for greater sensitivity in camera 80, and/or higher levels of discrimination in processing apparatus 82.

In another less preferred embodiment, infrared sensor 80 can be comprised of an array of individual infrared sensors sensing different but contiguous portions of underlying web 44 and separately reporting to processing apparatus 82 the energy so sensed, whereupon processing apparatus 82 develops the composite visual image from the multiple sensors.

In the environment of fabrication line 10, appropriate shielding, if needed, can be placed about infrared sensor 80 to prevent heat from nearby machinery from reaching the sensor and skewing the data being collected.

Infrared sensor 80 can be interfaced to processing apparatus 82 by known video formats such as NTSC, RS-170 and VGA formats. These formats enable image data to be sent from passive infrared sensor 80 in a form readable by process apparatus 82.

Process apparatus 82 comprises a computer module capable of comparing images from infrared sensor 80 with preselected image values stored in the computer or other memory storage device. One example of a processing apparatus 82 is the CHECKPOINT 800 (CVS-V816-000) produced by COGNEX of Natick, Mass., USA.

The computer module in processing apparatus 82 can process the infrared sensor input images and provide outputs therefrom. Signal processing of the images can develop and define various visual images and image signatures specifically associated with specific processes for fabricating various specific personal care articles 78 being sensed by sensor 80 or a corresponding sensor array. The signatures are generally defined by the amount of heat at various areas or zones of the personal care article precursors 45 of web 44.

The greater the amount of heat at a given portion of the web, the darker that portion of the web appears in the visual image. In general, sensor 80 is addressing a discrete length of the web, such as a length equal to 1–2 lengths of precursors 45 along the length of the web, at any given time. Along the length of web being sensed, sensor 80 senses the temperatures based on an array of signals received from discrete, closely spaced areas of the personal care articles being assessed in the web, and outputs signals, either serially or in tandem, representing the temperatures so sensed about the area being assessed.

The sensing of the temperatures at the closely spaced discrete locations can be done by taking a sequence of readings in serial order. In the alternative, the sensing at the closely spaced discrete locations can be done by taking the multiple temperature readings simultaneously, using a multiplicity of sensor elements. The method used for collecting the infrared data depends on the capability of the infrared instruments being used for data collection. Whichever data collection process is used, the multiple readings are combined in creating the visual image.

The signatures, namely the visual images, developed from the energy sensed, are sent to operator station 104 where the visual images are displayed on e.g. a computer screen, and are preferably also compared with expected and/or standard signatures of the respective personal care article products. Different products made according to different specifications, of course, have correspondingly different signatures. For example, in the embodiment of FIG. 3, processing apparatus 82 can send a signal to cull unit 102 to cull selected ones of personal care articles having improper signatures. Such improper signatures can be caused by an out-of-tolerance improper location of one sensed component relative to another sensed component. Other improper signatures can be caused by too little or too much heat being sensed at a certain position, for example representing too little adhesive, a glob of excess adhesive, or an ineffective ultrasonic bond.

Signatures having threshold levels of variance from target parameters suggest removal of the respective defective personal care articles 78 as by culling. Other signatures, showing lesser variances in one or more parameters of one or more components of a personal care article, can result in processing apparatus 82 sending signals to the various elements of fabrication line 10. Such signals can cause a controller inside or outside the respective device or unit to adjust the amount of adhesive being applied to respective components of web 44 and/or to adjust the positions of one or more components, such as leg elastics, containment flaps, or the like, being secured to underlying web 44, or e.g. the amount of pressure being applied at one or more of the nips.

In addition or in the alternative, signature variances can lead to out-of-tolerance warning signals, in addition to the routine visual image, being sent to an operator of the fabrication line machinery at operator station 104. The warning signal can be audible, visual, tactile, or any combination of signal expressions designed to gain the attention of the operator. Such a warning signal can display or announce, without limitation, the components identified as improper, the direction and degree of variance and/or proposed corrective action, so that the operator can make appropriate adjustments in the control system of the fabrication line.

The visual image on e.g. the computer monitor can be refreshed at any desirable frequency. Thus, the image can be continuously refreshed at the maximum rate of updated information available through sensor 80 and processing apparatus 82. In the alternative, the image can be refreshed only intermittently, such as once a minute, every 30 seconds, every 15 seconds, or at any other desired interval within the capacity of sensor 80 and processing apparatus 82.

While the description herein above, and the drawings, illustrate sensor 80 and processing apparatus 82 as separate and individual apparatus, the functions of sensor 80 and processing apparatus 82 can be incorporated into a single piece of equipment if desired, such that the signal processing unit is housed in a common housing or enclosure along with the sensing unit, as suggested by the dashed outline 106 about both sensor 80 and processing apparatus 82 in FIG. 1. Indeed, such combined housing can be beneficial in that the overall space required in the system layout, or floor plan footprint, may be reduced thereby.

In some embodiments, the outer surface of second layer 32 has visible figures or symbols printed thereon. Such printed visual figures or symbols are typically decorative in nature. While such printed visible figures or symbols interfere with product sensing using ultraviolet light or visible light for image sensing, such printed visible figures or symbols do not interfere with the ability of infrared sensor 80 to sense thermal properties of elements underlying the printed images, and thus effectively sees through such printed figures or symbols, thus to continue to generate accurate images of the infrared signature in spite of the printed visual figures or symbols.

FIGS. 4 and 5 illustrate cross-sections of precursors 45 of the invention. FIG. 4 illustrates the cross-section toward the rear of the personal care article precursor, showing absorbent core 20 and ear 46 in cross-section. FIG. 4 also shows bonds 90, 65 respectively at both inward 91 and outward 63 edges of containment flaps 56 outside the crotch region.

FIG. 5, by contrast, shows only the outward edges 63 of containment flaps 56 bonded by bonds 65 in underlying web 44, whereby inward edge 91 is free to stand up, away from second body-side liner layer 32 as illustrated in FIG. 6, and to interact directly with the body of the wearer when the personal care article is mounted on the body of a wearer. Further, FIG. 5 illustrates locations of containment flaps 56 and leg elastics 28 relative to the edges of leg cut-outs 96.

The invention has been described herein above in terms of incorporating a number of specific elements or characteristics into personal care articles, namely six specific elements (first layer 16, absorbent core 20, leg elastics 28, second layer 32, tapes 46, and containment flaps 56), plus adhesives, plus formation of ultrasonic bonds, in the fabrication process, to make personal care article precursors 45 and ultimately personal care articles 78. Any number of elements or characteristics can be used, as desired, in fabricating the personal care articles and wherein the invention comprehends assessing personal care articles so fabricated. Thus, as few as one element (for example bond location or bond strength) can be assessed. There is no upper limit to the number or type of elements or characteristics which can be assessed so long as the various elements or characteristics can be distinguished from each other on the visual image, or otherwise evaluated. Less than all relevant elements or characteristics can be assessed on a given visual image.

Referring to FIGS. 2, 7, and 8, the darker and wider the seal line on the visual image, generally the more secure the seal. Correspondingly, a relatively narrower and lighter seal line indicates a relatively weaker seal. A relatively wider and darker seal line indicates a relatively stronger seal. Accordingly, either processing apparatus 82, or an operator, can assess the strength of seals according to the combination of width and darkness of the seal on the visual image.

A plurality of infrared sensor elements can be combined into a single infrared sensor instrument, wherein the several sensor elements cooperate with each other in defining the composite visual image, e.g. the image displayed on monitor 81.

A plurality of infrared sensors 80 can be positioned at a corresponding plurality of locations along the length of the fabrication line 10. Such plurality of infrared sensors can all feed sensed data into a common processing apparatus 82. In the alternative, the plurality of sensors can feed sensed data into a plurality of processing apparatuses 82 (not shown), whereupon the plurality of processing apparatuses is coordinated by a master controller (not shown).

The invention has been illustrated herein as a quality assessment or manufacturing control tool. The invention can, as well, be used as a research and/or development tool for exploratory, non-destructive evaluation to support, for example, tests of new materials, new assemblies, new element arrangements, new arrangements of old elements, and the like.

Further, the invention has been illustrated herein as having advantage for sensing through a visually obstructive material which is, for example opaque, translucent, or occlusive or the like. The invention is equally operable, and useful to advantage for sensing infrared properties through clear, e.g. transparent materials which are emitting infrared energy as described above.

As used herein, an "element" of personal care article 78 or personal care article precursor 45 includes ultrasonic bonds and adhesive bonds, including adhesive employed for the purpose of making such bonds, as well as the tangible elements having relatively fixed dimensions such as absorbent core 20, tapes 46, and containment flaps 56.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A method of sensing assembly quality characteristics of a web of personal care article products or personal care article product precursors being fabricated on a fabrication line by processing apparatus, each personal care article product or personal care article product precursor having, as an element thereof, a bodyside liner, an outer cover, and at least one element of the personal care article product or personal care article product precursor disposed between the bodyside liner and the outer cover, the method comprising:
   (a) sensing infrared properties of product or product precursors being fabricated on the web using infrared sensing apparatus;
   (b) outputting signals indicative of infrared properties of the product or product precursors being fabricated on the web to visual image processing apparatus;
   (c) creating a database representative of infrared properties of product standards within selected control tolerance;
   (d) comparing the sensed infrared properties of product being fabricated with the database, using the image processing apparatus, the image processing apparatus comprising a programmable logic controller capable of comparing image data from the infrared sensing apparatus with preselected stored images of the database, and thereby developing an image comparison result; and
   (e) outputting processing adjustment signals from the programmable logic controller to processing apparatus of the fabrication line to effect adjustment of absorbent article processing in accord with the image comparison result.

2. A method as in claim 1 wherein signals indicative of infrared properties of product being fabricated on the web are outputted in video format acceptable for processing in the visual image processing apparatus.

3. A method as in claim 1, including outputting signals indicative of visual images, derived from the infrared signatures, to an operator station display using said visual image processing apparatus.

4. A method as in claim 3, including displaying at the operator station respective preselected stored visual image information on said operator station display concurrently with display of the real time images of infrared properties of product or product precursors being fabricated on the web.

5. A method as in claim 1, including comparing visual image data for a given personal care article on the web against a predetermined data standard and thereby determining conformance of the respective personal care article to the standard, and outputting cull signals to cull selected ones of such compared personal care articles from said fabrication line.

6. A method as in claim 1, including said visual image processing apparatus outputting one or more of the signals selected from the group consisting of:
   (i) a fabrication line shutdown signal;
   (ii) a signal which calls attention to characteristics of the personal care articles which are not within preselected control tolerances; and
   (iii) a signal which activates process adjustments to adjust characteristics of the personal care articles, such characteristics not being within preselected control tolerances before adjustment.

7. A method of fabricating composite personal care articles and sensing assembly quality characteristics of the personal care articles so fabricated, at least one of the components of precursors of the personal care articles so fabricated comprising a continuous web of material, the method comprising:
   (a) transporting the web along a fabrication line, past a plurality of work stations where work, for fabricating the personal care article precursors according to a predetermined arrangement, is performed on the web, thereby to form an array of precursors of such personal care articles on the web;
   (b) separating ones of the array of personal care article precursors, from the web, and into individual personal care articles, including severing the web across a transverse dimension thereof;
   (c) sensing infrared properties of product being fabricated on the web, and outputting signals indicative of infrared signatures of the product; and
   (d) accepting such outputted signals indicative of infrared signatures of the product being fabricated on the web, and processing such data and thereby determining assembly quality characteristics of respective ones of the composite personal care articles or composite personal care article precursors.

8. A method as in claim 7, including outputting such signals indicative of infrared signatures in video format acceptable for processing in visual image processing apparatus.

9. A method as in claim 7, further comprising, using a computer module, comparing image data from the infrared sensing apparatus with preselected stored images.

10. A method as in claim 7, further comprising outputting, from visual image processing apparatus, to an operator station display, output signals indicative of visual images and derived from the infrared signatures.

11. A method as in claim 10, further comprising concurrently displaying, at the operator station display, respective preselected stored visual image information.

12. A method as in claim 7, further comprising comparing image data for a given personal care article on the web against a predetermined data standard and thereby determining conformance of the respective personal care article to the standard, and outputting cull signals to cull selected ones of the compared personal care articles from the fabrication line.

13. A method as in claim 7, further comprising outputting, from the visual image processing apparatus, one or more signal from the group consisting of:
   (i) a fabrication line shutdown signal;
   (ii) a signal which calls attention to characteristics of personal care articles which are not within preselected control tolerances; and (iii) a signal which activates process adjustments to adjust characteristics of the personal care articles, such characteristics not being within preselected control tolerances before adjustment.

14. A method for fabricating composite personal care articles and sensing assembly quality characteristics of the personal care articles so fabricated, at least one of the components of precursors of the personal care articles so fabricated comprising a continuous web of material, the method comprising:
   (a) transporting the web along a fabrication line, past a plurality of work stations where work, for fabricating the personal care article precursors according to a predetermined arrangement, is performed on the web thereby to form an array of precursors of such personal care articles on the web;
   (b) separating ones of the array of personal care article precursors from the web, and into individual personal care articles, including severing the web across a transverse dimension thereof; and
   (c) sensing infrared signatures of product being fabricated on the web, thereby determining assembly quality characteristics of respective ones of the composite personal care articles or composite personal care article precursors, and outputting a signal representative of the sensed characteristics.

15. A method as in claim 14, further comprising receiving and processing such signal in a signal processor and providing a processor output representative of at least one of the personal care articles or personal care article precursors being fabricated on the fabrication line.

16. A method as in claim 14, further comprising placing an absorbent core on the web, and bodyside liner material over the absorbent core such that the absorbent core is between the web and the bodyside liner material and, using infrared sensing and signal processing apparatus, viewing and sensing the position of the absorbent core through visually obstructive material.

17. A method as in claim 14, further comprising placing an absorbent core on the web, and bodyside liner material over the absorbent core such that the absorbent core is between the web and the bodyside liner material, one of the bodyside liner and material of the web having a first surface facing infrared sensing and signal processing apparatus, the first surface having a visual printed image thereon, the method further comprising, using infrared sensing and signal processing apparatus, sensing an assembly quality characteristic under the respective one of the bodyside liner material and the web, through the visual printed image.

18. A method as in claim 14, further comprising applying adhesive for securing at least first portions of first respective components to second portions of second respective ones of the components and, using infrared sensing and signal processing apparatus, sensing one or both of the position of such adhesive in the personal care articles, and quantities of such adhesive in the personal care articles.

19. A method as in claim 14, further comprising placing absorbent cores over the web as elements of the personal care article precursors, the absorbent cores having zones comprising relative concentrations of superabsorbent and, using infrared sensing and signal processing apparatus, sensing the zones of relative concentration of superabsorbent as distinct from the remainders of the absorbent cores.

20. A method as in claim 14 further comprising, using an ultrasonic horn and cooperating anvil, providing ultrasonic energy to create bonds bonding, in the personal care article precursors, at least one component of such personal care article precursors and, using infrared sensing and signal processing apparatus, sensing the positions of such ultrasonic bonds.

21. A method as in claim 20, further comprising providing output from the infrared sensing and signal processing apparatus to an operator station as an indication when the infrared sensing and signal processing apparatus does not detect the presence of the ultrasonic bonds.

22. A method as in claim 14 further comprising, using infrared sensing and signal processing apparatus, sensing registration of predetermined ones of the components.

23. A method as in claim 14, further comprising sending an alarm signal as an output of an infrared sensing and signal processing apparatus to an operator station, and thereby identifying existence of an improper condition for at least one of the components.

24. A method as in claim 14, further comprising outputting a cull signal from the infrared sensing and signal processing apparatus, to cull selected one or more of the personal care articles from the fabrication line.

25. A method as in claim 14, further comprising outputting, from the infrared sensing and signal processing apparatus, one or more signal selected from the group consisting of:
   (i) a fabrication line shutdown signal;
   (ii) a signal which calls attention to characteristics of personal care articles which are not within preselected control tolerances; and
   (iii) a signal which activates process adjustments to adjust characteristics of the personal care articles, such characteristics not being within preselected control tolerances before adjustment.

26. A method as in claim 14 further comprising, using infrared sensing and signal processing apparatus, sensing assembly quality characteristics common to personal care articles being fabricated on the fabrication line, the assembly quality characteristics, in combination, comprising a signature for the personal care articles being fabricated.

27. A method as in claim 14 further comprising, using infrared sensing and signal processing apparatus, sensing portions of personal care articles being fabricated on the fabrication line and having temperatures as low as about 20 degrees Celsius and up to about 200 degrees Celsius.

28. A method as in claim 14 further comprising, using a passive infrared sensor, sensing temperature differences across an overall projected surface defined by an area of one of the personal care articles.

29. A method as in claim 14 further comprising, using an infrared camera, collecting infrared images from the personal care articles.

30. A method as in claim 14 further comprising, using infrared sensing and signal processing apparatus, outputting a composite visual image representative of at least one of the personal care articles or personal care article precursors.

31. A method as in claim 30, further comprising collecting, for each visual image, an array of infrared signals from discrete areas of the personal care articles being assessed.

32. A method as in claim 14, further comprising outputting, from infrared sensing and signal processing apparatus, a signal representing an out-of-tolerance condition in the personal care article or personal care article precursor sensed, and sending the out-of-tolerance signal to an operator station.

* * * * *